United States Patent
McCombie et al.

(10) Patent No.: US 8,313,439 B2
(45) Date of Patent: Nov. 20, 2012

(54) CALIBRATION OF PULSE TRANSIT TIME MEASUREMENTS TO ARTERIAL BLOOD PRESSURE USING EXTERNAL ARTERIAL PRESSURE APPLIED ALONG THE PULSE TRANSIT PATH

(75) Inventors: Devin B. McCombie, Solana Beach, CA (US); Haruhiko H. Asada, Lincoln, MA (US); Andrew T. Reisner, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 756 days.

(21) Appl. No.: 12/408,345

(22) Filed: Mar. 20, 2009

(65) Prior Publication Data

US 2010/0241011 A1    Sep. 23, 2010

(51) Int. Cl.
  *A61B 5/02*    (2006.01)
(52) U.S. Cl. ........ 600/485; 600/481; 600/483; 600/486; 600/488; 600/500
(58) Field of Classification Search .......... 600/485, 600/481, 301, 483, 486, 488, 500–504
See application file for complete search history.

(56) References Cited

U.S. PATENT DOCUMENTS

| | | | |
|---|---|---|---|
| 4,524,777 A | 6/1985 | Kisioka et al. | 128/677 |
| 4,846,189 A | 7/1989 | Sun | 600/492 |
| 4,869,262 A | 9/1989 | Orr et al. | 128/672 |
| 5,111,826 A | 5/1992 | Nasiff | 128/672 |
| 5,152,297 A | 10/1992 | Meister et al. | 128/672 |
| 5,183,051 A | 2/1993 | Kraidin et al. | 128/687 |
| 5,241,964 A * | 9/1993 | McQuilkin | 600/485 |
| 5,309,916 A | 5/1994 | Hatschek | 128/672 |
| 5,533,511 A | 7/1996 | Kaspari et al. | 128/672 |
| 5,712,926 A | 1/1998 | Eberhard et al. | 382/205 |
| 5,778,879 A | 7/1998 | Ota et al. | 128/672 |
| 5,865,755 A * | 2/1999 | Golub | 600/485 |
| 5,995,859 A | 11/1999 | Takahashi | 600/323 |
| 6,280,390 B1 | 8/2001 | Akselrod et al. | 600/485 |
| 6,322,515 B1 | 11/2001 | Goor et al. | 600/485 |

(Continued)

FOREIGN PATENT DOCUMENTS

WO    WO 98/04182    2/1998

(Continued)

OTHER PUBLICATIONS

McCombie, D.B.; Shaltis, P.A.; Reisner, A.T.; Asada, H.H.; , "Adaptive hydrostatic blood pressure calibration: Development of a wearable, autonomous pulse wave velocity blood pressure monitor," Engineering in Medicine and Biology Society, 2007. EMBS 2007. 29th Annual International Conference of the IEEE , vol., no., pp. 370-373, Aug. 22-26, 2007.*

(Continued)

*Primary Examiner* — Charles A Marmor, II
*Assistant Examiner* — Sunita Reddy
(74) *Attorney, Agent, or Firm* — Sunstein Kann Murphy & Timbers LLP (57) ABSTRACT

An apparatus and methods for adaptive and autonomous calibration of pulse transit time measurements to obtain arterial blood pressure using arterial pressure variation. The apparatus and methods give pulse transit time (PTT) devices an ability to self-calibrate. The methods apply a distributed model with lumped parameters, and may be implemented, for example, using pulse transit time measurements derived from a wearable photoplethysmograph (PPG) sensor architecture with an intervening pressurizing mechanism.

20 Claims, 10 Drawing Sheets

U.S. PATENT DOCUMENTS

| | | | |
|---|---|---|---|
| 6,537,225 B1 | 3/2003 | Mills | 600/481 |
| 6,592,528 B2 | 7/2003 | Amano | 600/485 |
| 6,647,287 B1* | 11/2003 | Peel et al. | 600/513 |
| 6,932,772 B2 | 8/2005 | Kan | 600/490 |
| 7,014,611 B1 | 3/2006 | Geddes et al. | 600/490 |
| 2002/0169381 A1 | 11/2002 | Asada et al. | 600/485 |
| 2002/0777781 | 11/2002 | Amano | 600/485 |
| 2004/0024326 A1 | 2/2004 | Yeo et al. | 600/500 |
| 2004/0162493 A1 | 8/2004 | Mills | 600/481 |
| 2005/0096557 A1 | 5/2005 | Vosburgh et al. | 600/509 |
| 2005/0215912 A1 | 9/2005 | Freund et al. | 600/485 |
| 2005/0261593 A1* | 11/2005 | Zhang et al. | 600/485 |
| 2006/0074322 A1* | 4/2006 | Nitzan | 600/485 |
| 2006/0195034 A1 | 8/2006 | Skrabal et al. | 600/485 |
| 2007/0055163 A1* | 3/2007 | Asada et al. | 600/485 |
| 2008/0039731 A1* | 2/2008 | McCombie et al. | 600/485 |
| 2008/0221461 A1* | 9/2008 | Zhou et al. | 600/485 |

FOREIGN PATENT DOCUMENTS

| | | |
|---|---|---|
| WO | WO 98/25511 | 6/1998 |
| WO | WO 03/039326 | 5/2003 |

OTHER PUBLICATIONS

Asada et al. *"Mobile Monitoring with Wearable Photoplethysmographic Biosensors,"* IEEE Engineering in Medicine and Biology Magazine, vol. 22(3), pp. 28-40, May/Jun. 2003.

Shaltis et al. *"A Hydrostatic Pressure Approach to Cuffless Blood Pressure Monitoring,"* 2004 26th Annual International Conference of the IEEE/EMBS, San Francisco, CA, USA, Sep. 1-5, 2004.

Shaltis et al. *"Calibration of the Photoplethysmogram to Arterial Blood Pressure: Capabilities and Limitations for Continuous Pressure Monitoring,"* 2005 27th Annual International Conference of the IEEE/EMBS, Shanghai, China, Sep. 1-4, 2005.

Asada et al. *"Towards the Development of Wearable Blood Pressure Sensors: A Photo-Plethysmograph Approach,"* Mini-Symposium, 2005 27th Annual International Conference of the IEEE/EMBS, Shanghai, China, Sep. 1-4, 2005.

Shaltis et al. *"Novel Design for a Wearable, Rapidly-Deployable, Wireless Noninvasive Triage Sensor,"* 2005 27th Annual International Conference of the IEEE/EMBS, Shanghai, China, Sep. 1-4, 2005.

Reisner et al. *"A Miniaturized Device Capable of Near-Imperceptible Function: Toward a Wearable Monitor for Continuous Arterial Blood Pressure,"* 2006 MGH Scientific Advisory Committee Research Symposium, Feb. 17, 2006.

Shaltis et al. *"Wearable, Cuff-less PPG-Based Blood Pressure Monitor with Novel Height Sensor,"* 2006 28th Annual International Conference of the IEEE/EMBS, New York, New York, Aug. 30-Sep. 3, 2006.

Penaz, J. *"Photoelectric Measurement of Blood Pressure, volume and Flow in the Finger,"* Digest of the 10th International Conference on Medical and Biological Engineering, Session 7, p. 104, 1973.

Teng et al. *"Continuous and Noninvasive Estimation of Arterial Blood Pressure Using a Photoplethysmographic Approach,"* Proceedings of the $25^{th}$ Annual International Conference of the IEEE EMBS, pp. 3153-3156, Sep. 17-21, 2003.

Kamakoshi et al. *"Current Developments in non-invasive measurement of arterial blood pressure,"* J. Biomed. Eng. vol. 10, pp. 130-137, Apr. 1988.

Kamakoshi et al. *"Long-term ambulatory monitoring of indirect arterial blood pressure using a volume-oscillometric method,"* Med. & Biol. Eng. & Comput., vol. 23, pp. 459-465, 1985.

International Search Report, dated Jan. 19, 2007; received Jan. 23, 2007; PCT/US2006/032601.

International Search Report, dated Apr. 4, 2007; received Apr. 17, 2007; PCT/US2006/045590.

O'Rourke (ed.) *"Properties of the arterial wall: theory",* McDonald's Blood Flow in Arteries: Theoretical Experimental & Clinical Principles, Oxford U. Press, pp. 54-72, 1997.

United States Patent and Trademark Office Office Action dated Dec. 8, 2008 in corresponding U.S. Appl. No. 11/508,123—8 pages.

McCombie et al. "Adaptive Blood Pressure Estimation from Wearable PPG Sensors Using Peripheral Artery Pulse Wave Velocity Measurements and Multi-Channel Blind Identification of Local Arterial Dynamics," *Proceedings of the $28^{th}$ IEEE, EMBS Annual International Conference*, pp. 3521-3524 (2006).

Teng "Theoretical Study on the Effect of Sensor Contact Force on Pulse Transit Time," *IEEE Transactions on Biomedical Engineering*, vol. 54, No. 8, pp. 1490-1498 (2007).

\* cited by examiner

CALIBRATION OF PULSE TRANSIT TIME MEASUREMENTS TO ARTERIAL BLOOD PRESSURE USING EXTERNAL ARTERIAL PRESSURE APPLIED ALONG THE PULSE TRANSIT PATH

TECHNICAL FIELD

The present invention relates to methods and apparatus for adaptive and autonomous calibration of pulse transit time measurements to obtain arterial blood pressure using arterial pressure variation. This methodology, applying a distributed model of a pulse transit path, gives pulse transit time (PTT) devices the ability to self-calibrate, and may be implemented using a wearable photoplethysmograph (PPG) sensor architecture.

BACKGROUND OF INVENTION

High blood pressure, or hypertension, is a major health problem in America an estimated 72 million adults suffer from this condition in the United States. The problem is even greater worldwide.

Feedback from a non-invasive monitor has been shown to improve patient compliance with prescribed treatment regimens. Additionally, a person's blood pressure is not constant throughout the day and is known to exhibit a circadian rhythm. Twenty four hour ambulatory blood pressure monitoring has been shown to be a valuable tool in predicting cardiovascular events.

Leading non-invasive home and hospital blood pressure monitors, however, are not well-suited for non-invasive monitoring because, in that they are based on oscillometry and sphygmomanometery, they rely on inflation of an obtrusive cuff to estimate blood pressure (BP). These cuff based devices require occlusion of the artery being monitored through cuff inflation which increases the external pressure acting on the artery above the systolic blood pressure. During BP measurement, these types of actuated monitors are uncomfortable and interfere with the wearer's daily routine by requiring an irksome measurement period.

A passive, non-invasive blood pressure monitoring alternative exists in devices that measure arterial pulse wave velocity or pulse transit time (PTT). Although this method offers the potential for passive beat-to-beat blood pressure estimation, it has found limited use in home and hospital BP monitoring due to inherent drawbacks in the existing technology.

PTT-based devices are deficient in that they are incapable of autonomous calibration. Typically, a traditional cuff based device is required to calibrate the patient-specific relationship between PTT and BP prior to their use. The relationship between PTT and BP is governed by a number of vascular properties; chief among these is the compliance of the artery. The PTT/BP relationship is discussed in Nichols & O'Rourke, *McDonald's Blood Flow in Arteries: Theoretical, Experimental, and Clinical Principles*, (4th ed., London, 1998), chap. 3, which is incorporated herein by reference.

The compliance of skeletal arteries may be altered by both central and local cardiovascular control mechanisms, as discussed, for example by Guyton & Hall, *Textbook of Medical Physiology*, (9th ed., 1996), chap. 18, which is incorporated herein by reference. Use of a fixed, predetermined calibration model can result in significant BP estimation error using PTT measurements if the cardiovascular state of the patient changes.

SUMMARY OF INVENTION

In accordance with preferred embodiments of the present invention, methods and apparatus are provided for autonomous calibration of a pulse-transit-time monitoring device for measurement of arterial blood pressure. A preferred embodiment of the method has steps of:

measuring a pulse transit time of a circulatory feature between a proximal sensor position and a distal sensor position, the proximal and distal sensor positions disposed along a single arterial transit path on a human body;

parameterizing a modeled quantitative relationship among a set of quantities, at least one of which quantities is a quantity distributed with distance along the transit path;

performing a measurement so as to provide a plurality of quantities from among the set of quantities; and solving the plurality of quantities, on the basis of the modeled quantitative relationship, so as to obtain the arterial blood pressure as a function of the measured pulse transit time.

In accordance with other embodiments of the invention, the quantity distributed with distance along the transit path may parameterized as a function of external pressure, and may be treated as a function that is invariant over the transit path. More particularly, the quantity distributed with distance may be arterial stiffness, and it may be parameterized as a function of transmural pressure, pulse wave velocity, arterial blood pressure, vertical height of all loci along the transit path, and any external pressure on a body surface along the transit path.

The step of measuring may include measuring a pressure, and, in particular, an externally applied pressure. The step of solving may include deriving a general dynamic relationship s(t) between a change in external pressure $\Delta P_{ex}(t)$, applied to an artery wall between the proximal sensor position and the distal sensor position, and a resulting change in pulse transit time $\Delta PTT(t)$.

The set of quantities, the relationship among which is the subject of the model, may include a plurality of quantities selected from the group including transmural pressure, pulse wave velocity, arterial blood pressure, vertical height of a plurality of loci along the transit path, and any external pressure on a body surface along the transit path. The transit path may be treated in a lumped parameter model having at least three segments with respect to evaluation of the at least one quantity distributed with distance along the transit path. The positions of each of the sensors may constitute segments of the model in their own right. In some embodiments of the invention, the vertical height of all the segments may be considered to be equal.

In accordance with alternate embodiments of the invention, the method may have a further step of externally varying the transmural pressure at least at one position along the arterial path connecting the proximal sensor position and the distal sensor position by virtue of applying an external pressure.

In other embodiments, the quantified relationship may be computed while the segments of the arterial path are moved through a plurality of heights, and the pulse transit time may be remeasured pulse transit time to eliminate the at least one model variable to obtain a calibrated measure of arterial blood pressure. The transmural pressure may be varied at one of the sensor positions, and/or, by means of a cuff, or other pressurizing element. The pressure may also be varied by varying body posture, such as the position of the wrist.

In accordance with another aspect of the present invention, an apparatus is provided for performing a circulatory measurement on an extremity of a subject. The apparatus has two sensors, each disposed at a different position along a single arterial path on the extremity of the subject. Additionally, the apparatus has a pressurizing mechanism for varying a transmural pressure at a specified position along the single arterial path between the first and second positions. Finally, the apparatus has a processor for obtaining the circulatory measurement based on a measured transit time and the distance between the first and second positions and a calibration relating the circulatory measurement to the measured transit time on the basis of at least two distinct pressures applied by virtue of the pressuring mechanism.

In accordance with yet another aspect of the present invention, an apparatus is provided for performing a circulatory measurement on an extremity of a subject. The apparatus has two sensors, each disposed at a different position along a single arterial path on the extremity of the subject. Additionally, the apparatus has a pressure sensor for measuring external pressure at least at a specified position along the single arterial path between the sensors, and a processor for obtaining the circulatory measurement based on a measured pulse transit time and a calibration relating the circulatory measurement to the measured transit time on the basis of the measured external pressure and a mathematical model of the arterial path.

BRIEF DESCRIPTION OF THE DRAWINGS

Advantages of the present invention and its several improvements will be seen when the following detailed description is read in conjunction with the attached drawings. These drawings are intended to provide a better understanding of the present invention, but they are in no way intended to limit the scope of the invention.

DETAILED DESCRIPTION OF PREFERRED EMBODIMENTS

In accordance with preferred embodiments of the present invention, a novel calibration tool is provided for determining the relationship between pulse transit time and arterial blood pressure. This new calibration methodology eliminates the need for an oscillometer or syphgmomanometer for calibration. Moreover, it provides PTT devices with a means to adaptively identify the parameters of a calibration model directly during their measurement period. This new calibration technique identifies the parameters of a model relating pulse transit time to arterial blood pressure by altering an external arterial pressure acting on a segment of the arterial transit path through a change in the skin contact pressure applied by the device to tissue surrounding the arterial wall. The change in external pressure results in a measured change in PTT that is used to determine the parameters of the calibration model. Related methods are discussed in McCombie et al., "Motion Based Adaptive Calibration of Pulse Transit Time Measurements to Arterial Blood Pressure for an Autonomous, Wearable Blood Pressure Monitor," in *Proc. 30th IEEE Int. Conf. Engineering in Medicine and Biology*, (Vancouver, 2008), which is incorporated herein by reference.

While PTT has been used to track trends in BP, there has been no explicit solution, nor application to advantage, of external pressure, i.e., pressure applied on the skin surface by a sensor, and no recognition that external pressure can alter PTT even if BP stays the same. This is because external pressure can counteract the intra-arterial pressure, decompressing the artery, increasing its compliance, and thus increasing PTT).

In accordance with embodiments of the invention, the arterial path is treated like a distributed system, with a consistent functional relationship for the different segments. By assuming that the same functional relationship governs the distinct segments, the number of unknown parameters is minimized which opens up an innovative practical method of using PTT to measure and track BP. In certain embodiment, the specific formula explicitly considers the effects of BP, external pressure, the elastic properties of the artery, and of gravity, and offers a method of identifying all the unknown parameters, yielding BP and an explicit relationship between BP and PTT. In alternative embodiments, some of the parameters, e.g. surface pressure, are directly measured by sensors, yielding BP or at least a quantitative relationship between BP and PTT (so that BP trends can be estimated from PTT trends).

One advantageous feature of the present invention is that the external pressure required for the calibration of PTT can be much less than the patient's systolic blood pressure. A change in external pressure may be applied to the artery with either an actuated cuff or band or with a self adjusting device implemented by a healthcare worker or by the patient themselves.

Calibration by Means of an Externally Applied Arterial Pressure

Figure 1:
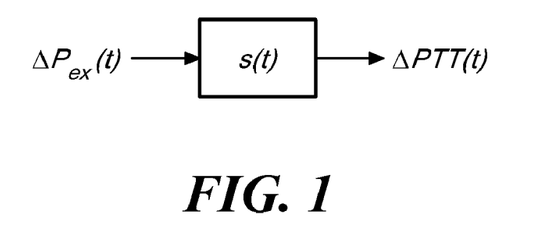
FIG. 1 is a block diagram depicting the relationship between external arterial pressure and pulse transit time in accordance with an embodiment of the invention.

In accordance with certain embodiments of the invention, an external pressure may be applied to an artery wall along the pulse transit path that is being monitored by a pair of sensors and the applied external pressure may be used as a tool to predictably alter measured pulse transit time. This modality is depicted in the block diagram in FIG. 1, where s(t) represents a general dynamic relationship between the change in external pressure $\Delta P_{ex}(t)$, applied to the artery wall and the resulting change in pulse transit time $\Delta PTT(t)$. In accordance with various embodiments of the invention described herein, a pressure may be sensed, by means of a pressure sensor, or a pressure may be applied, at a position along the pulse transit path, inclusive of the endpoints of the path. Thus, as used herein, the term "between" shall be understood to be inclusive of the endpoints.

Demonstration of the Physiological Phenomenon

Variation in pulse wave velocity with skin contact force along an arterial segment underlying a PPG sensor housing has been described by Teng and Zhang, "Theoretical Study on the Effect of Sensor Contact Force on Pulse Transit Time," IEEE Trans. Biomed. Eng., vol. 54, pp. 1490-1498 (August, 2007), incorporated herein by reference. Teng and Zhang proposed that external pressure applied to the digital arteries by finger tip PPG sensor reduced transmural pressure in the these arteries which in turn increased the pressure dependent compliance of the arterial wall and lowered the pulse wave velocity through the pressurized arterial segment. Their pulse arrival time estimates were determined as the timing difference between the peak of the QRS complex (representing ventricular depolarization) of the EKG waveform and the onset of a PPG waveform measured at the fingertip. Their conclusion was that this phenomenon was a potential source of error in their blood pressure estimates using their measured pulse arrival time.

In this section, it is shown how external pressure applied to the skin causes a change in pulse transit time that is a function of arterial compliance. Moreover, it shown that the application of external pressure need not be merely a potential source of error, as taught in the prior art, but that it may be used advantageously, in accordance with the present invention, for calibrating pulse transit time measurements to arterial blood pressure.

A set of experiments were performed to evaluate the effect that the external pressurization of a segment of the pulse transit path has on the velocity of the propagating pressure pulse along the arterial path being monitored by a pair of sensors, a proximal sensor and a distal sensor. The experimental protocol was as follows; an EKG signal, a PPG signal which was derived from the ulnar artery at the left wrist, and a digital artery PPG signal derived at the base of the little finger of the left hand were measured simultaneously. Both the wrist and finger PPG sensors were attached to the subject with an elastic band which caused the plastic sensor housings that contained the sensor components to exert contact pressures to the skin surface at the two measurement sites, at the wrist: $P_w(t=0)$, and at the finger: $P_f(t=0)$, respectively.

Figure 2:
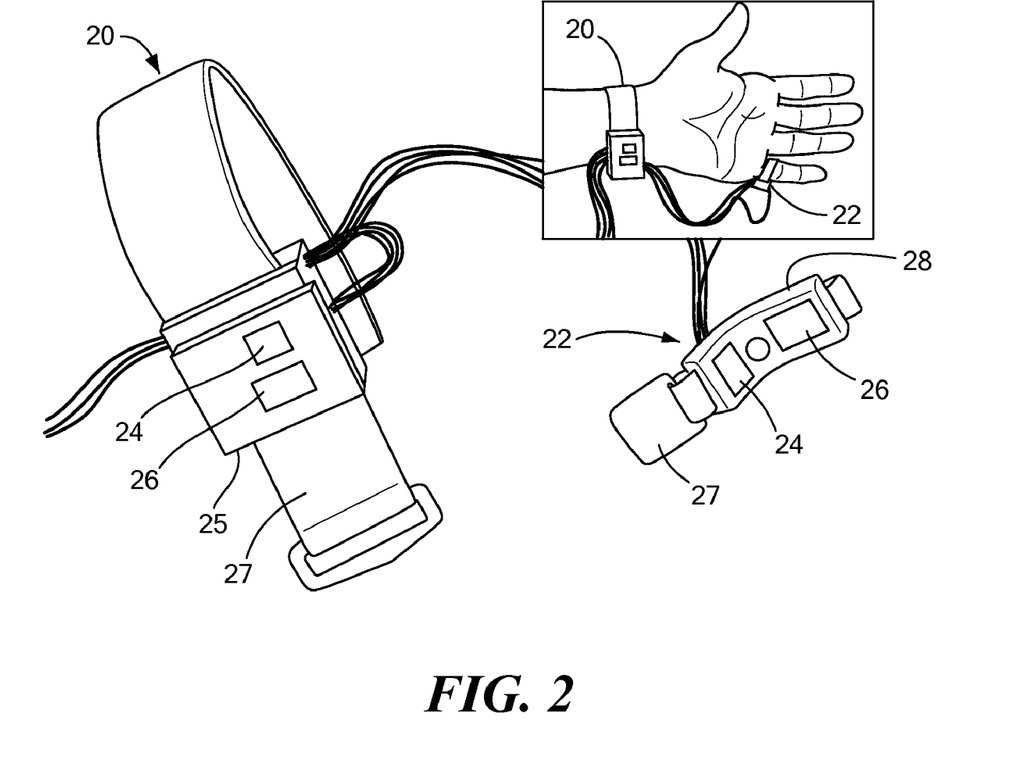
FIG. 2 shows a pulse transit time measurement device employing twin-PPG sensors, in accordance with an embodiment of the present invention.

The contact pressure exerted by the sensor housings caused an increase in the external pressure being applied to the wall of the arterial segment underlying the sensor housings. Two PPG sensors, a proximal sensor 20 and a distal sensor 22, are shown in FIG. 2. In the embodiment illustrated by way of example, proximal sensor 20 is a wristwatch sensor, and distal sensor 22 is a ring sensor. Each of the sensors is a photoplethysmographic sensor, illustrated by way of example, and each has a source 24 of light (in this case, a light-emitting diode (LED)) and a photodetector 26. Throughout the experiment the left arm was supported in a fixed position. The experiment was separated into two different stages: throughout stage one of the experiment (0<t<30 sec.), PPG and EKG measurements were collected with the external contact pressure of the wrist and finger PPG sensor held constant at the initial pressure provided by the elastic bands 27. At the onset of stage two of the experiment (t=30 sec.), the external sensor pressure $P_w(t)$, applied by the wrist sensor to the measurement site was increased by applying a direct force to the sensor housing 25. This direct force was held constant and applied throughout stage two of the experiment (30 sec.<t<60 sec.). Care was taken to keep the external wrist sensor pressure below the mean arterial pressure through observation of the wrist PPG waveform morphology. The external pressure applied by the finger sensor housing 28 was held constant at the initial stage 1 pressure during stage 2.

The change in pulse transit time between the two stages was observed in PTT measurements estimated from the difference of the arrival time of the finger PPG waveform minimum and the peak time of the QRS complex of the EKG waveform. This allowed for an evaluation of the effect on PTT produced by an increase in wrist sensor contact force by increasing the external pressure along a segment of the arterial path leading to the finger PPG signal, while the contact pressure of the finger sensor used to estimate pulse onset was not varied. If the magnitude and morphology of the finger PPG signal remain constant across both stages of the experiment, then it may be inferred that an increase in pulse transit time must be the result of a decrease in pulse wave velocity through the externally pressurized arterial segment.

Figure 3:
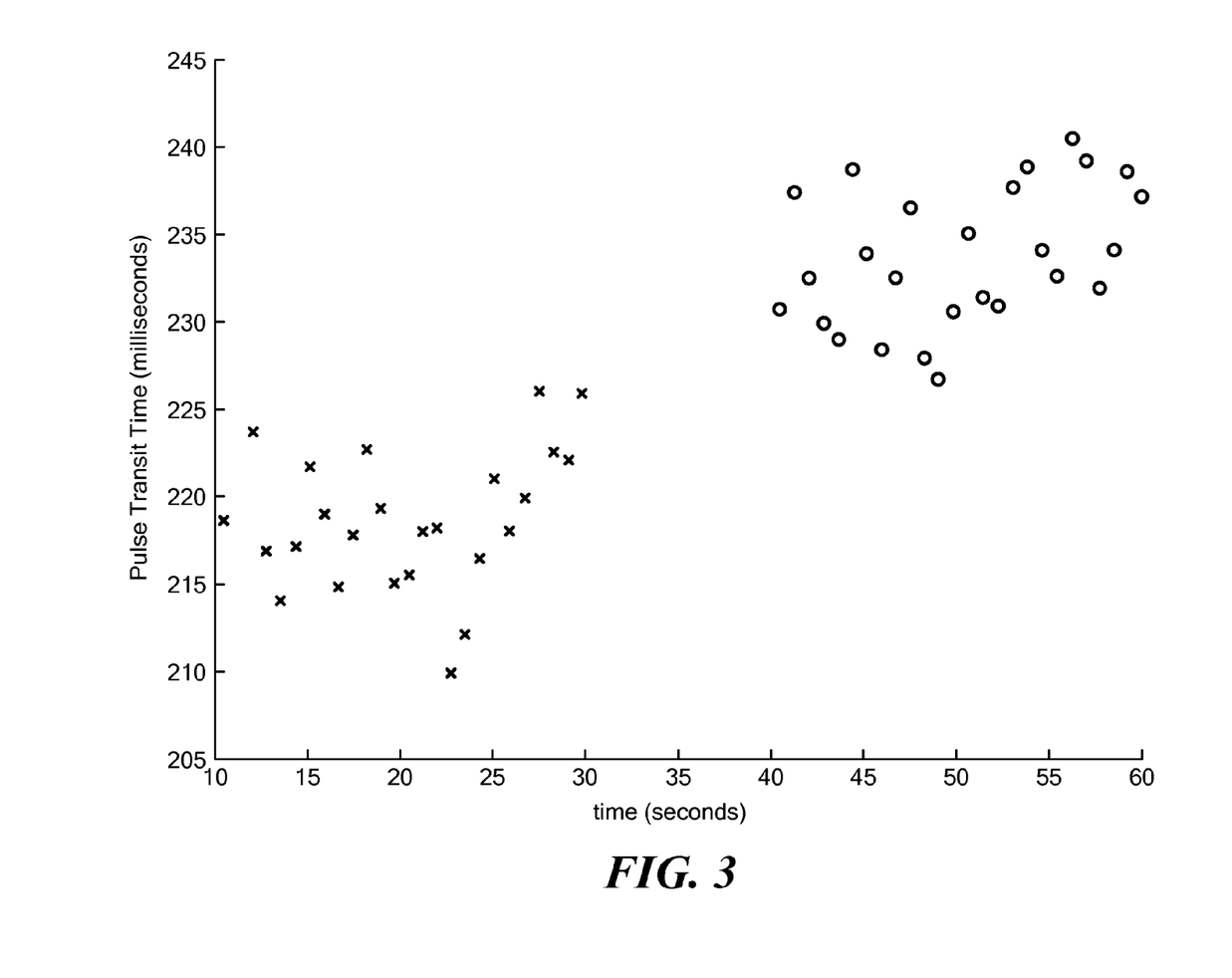
FIG. 3 is a scatter plot of pulse transit time estimates for a male subject derived from the EKG and finger PPG before (t<30 sec.) and after (t>30 sec.) direct wrist sensor pressurization.

A sample experimental result of the pulse transit times measured between the finger PPG and EKG before and after wrist sensor pressurization for a healthy male subject is shown in FIG. 3. To simplify data processing and to eliminate any transient effects that may occur due to subject movement during the start of the experiment and immediately following external pressurization of the wrist sensor, measurements from the first 10 seconds of each stage were discarded. Stage 1 ptt measurements are displayed in FIG. 3 using an "x" and stage 2 ptt measurements are displayed using a "o".

A 15 millisecond increase was observed in the mean PTT following pressurization of the wrist sensor, changing from a mean stage 1 PTT of 218.7 milliseconds to a mean stage 2 ptt of 233.7 milliseconds. The change in PTT observed following housing pressurization was directly correlated with the change in external pressure in the arterial segment underlying the housing.

Figure 4:
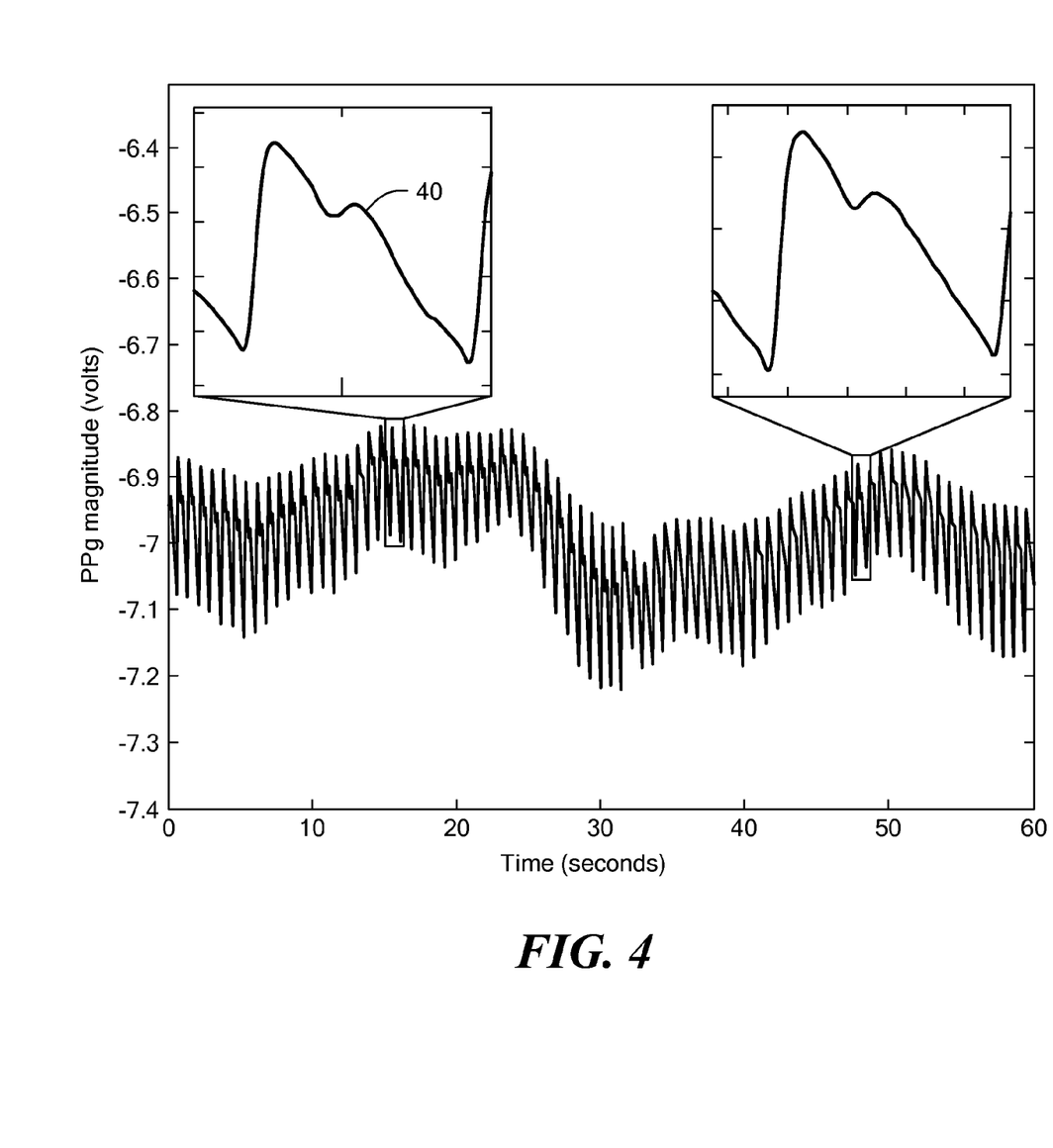
FIG. 4 shows a measured finger PPG signal before (t<30 sec.) and after (t>30 sec.) direct wrist sensor pressurization in accordance with an embodiment of the invention.
Figure 5:
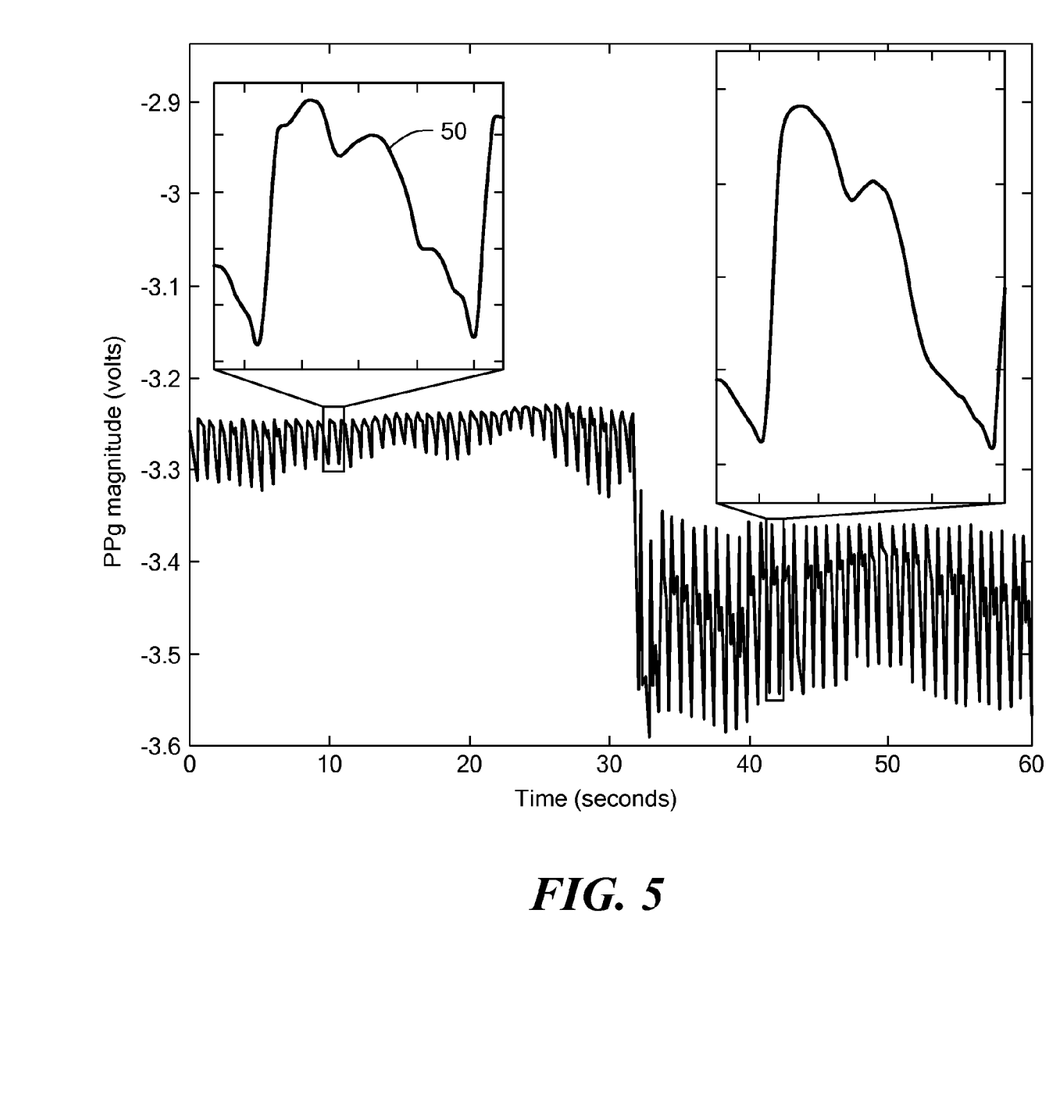
FIG. 5 shows a measured wrist PPG signal before (t<30 sec.) and after (t>30 sec.) direct wrist sensor pressurization, in accordance with an embodiment of the invention.

The finger PPG signal and wrist PPG signal measured during this experiment are shown in FIGS. 4 and 5, respectively. The change in mean finger PPG magnitude between the two stages was less than 3% or 8 millivolts and the morphology of the finger PPG before and after pressurization remains essentially constant as shown in the figure. In contrast to the finger PPG signal 40, the wrist PPG signal 50 undergoes a significant change in both magnitude exhibiting a nearly 300% increase a change of 100 millivolts and waveform morphology following pressurization of the wrist sensor housing.

The behavior demonstrated in the sample experiment shown in these figures was typical of the wrist sensor pressurization response observed in the PTT measurements derived from the finger PPG and EKG waveform.

The direct correlation between pulse transit time change and external pressure change was consistently demonstrated in multiple tests performed on different subjects. The average of three test results for a healthy male test subject (Patient 1) and healthy female test subject (Patient 2) are displayed in Table 1.

An additional relationship that can be observed in the data in Table 1 was the correlation between mean arterial pressure and the magnitude of the pulse transit time change caused by increasing external pressure at the wrist sensor. This behavior can be attributed to an ability to apply a larger external pressure change in an individual with a higher mean pressure while still maintaining the external pressure at or below the level of the mean arterial pressure.

TABLE 1

Average pulse transit time values before (stage 1) and after (stage 2) wrist sensor pressurization derived from three Direct Pressure EKG Test performed on two different patients

|  | Patient 1 | Patient 2 |
| --- | --- | --- |
| Mean $ptt_1$ (msec) | 217.6 | 229.9 |
| Mean $ptt_2$ (msec) | 233.3 | 235.2 |
| Mean $\Delta ptt$ (msec) | 15.7 | 5.2 |
| $\sigma_{ptt}$ (msec) | 1.1 | 1.5 |
| Change in finger PPG magnitude | 9.1% | 13.5% |
| Mean arterial pressure (mmHg) | 101 | 73 |

Figure 6:
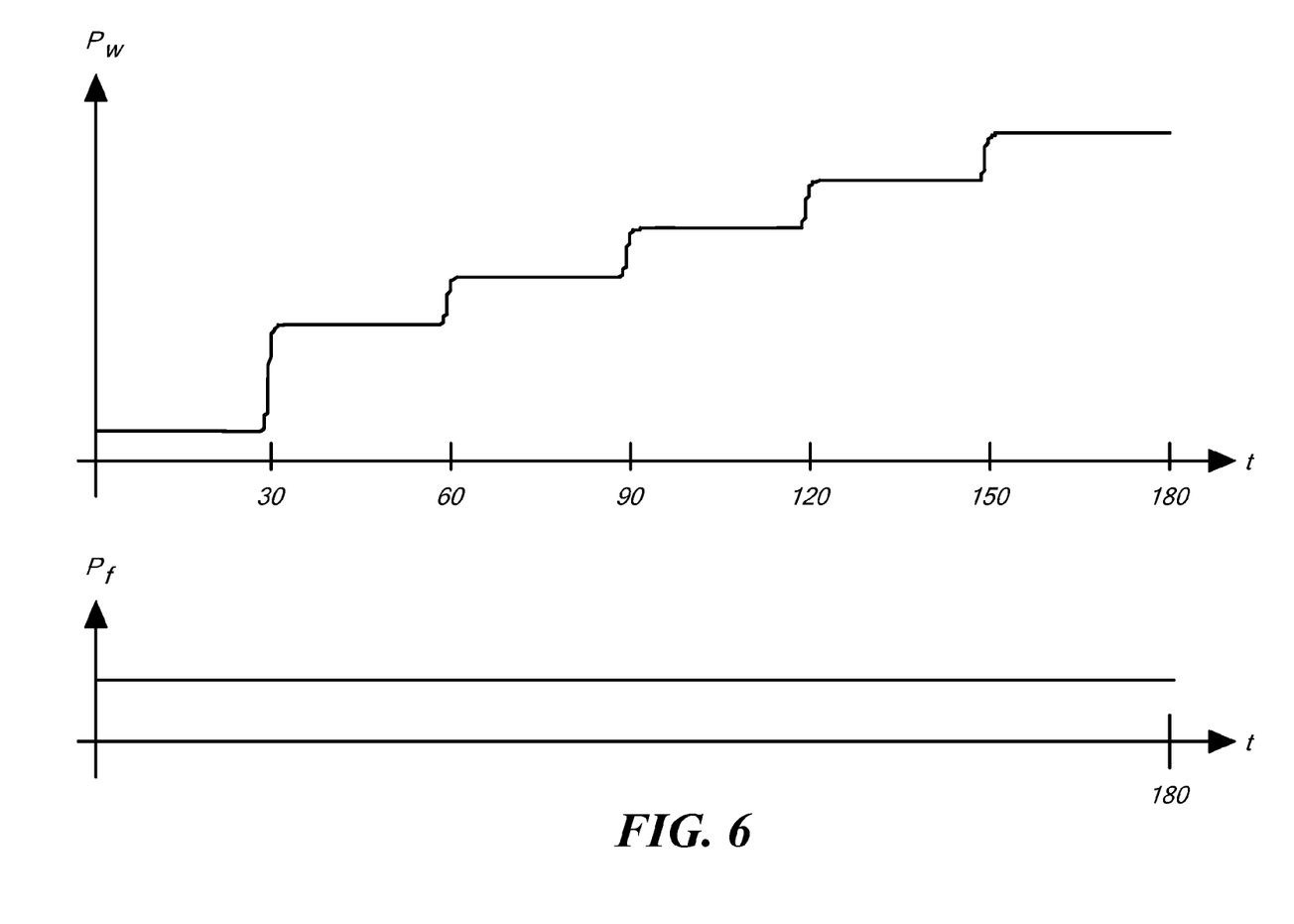
FIG. 6 shows multi-stage variation in external wrist sensor pressure using direct pressure applied to the wrist sensor housing in accordance with an embodiment of the invention.

The relationship between external sensor force, arterial blood pressure, and pulse transit time was investigated further by observing the effects of multiple step changes in sensor contact force on pulse transit time measurements and PPG magnitude. The experimental protocol used in these tests was similar to the two-stage test described in the previous experiment. However, instead of limiting the experiment to two external pressure stages the test consisted of 6 different stages in which contact force on the wrist sensor was increased at each successive stage and held constant for a 30 second period. A sketch of the external sensor pressures implemented in the protocol is shown in FIG. 6.

Figure 7:
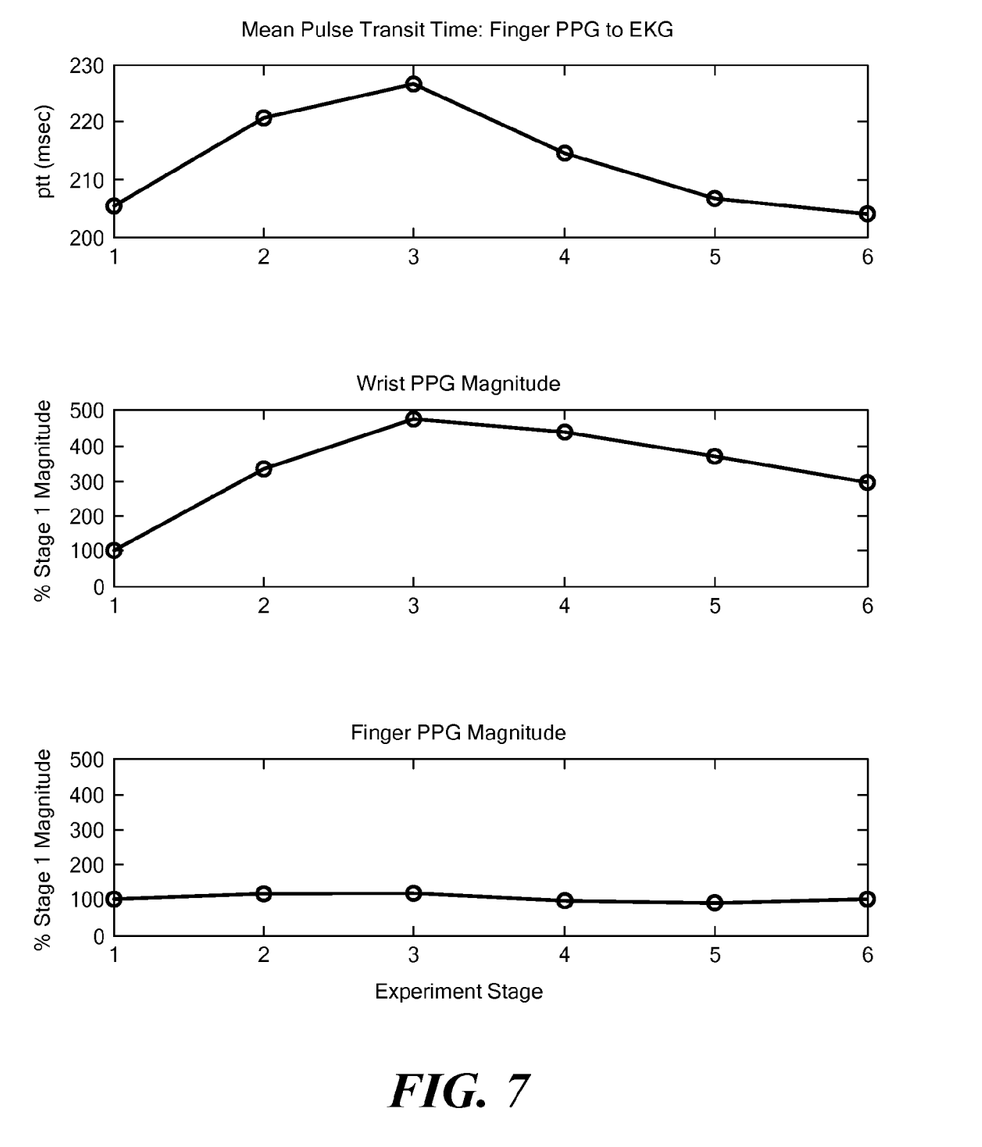
FIG. 7 shows pulse transit time and PPG magnitudes for a healthy male subject in response to a multi-stage increase in external wrist sensor pressure, as measured in accordance with an embodiment of the invention.

Pulse transit times were estimated during each stage as the timing difference between the minimum of the finger PPG waveform and the peak of the QRS complex of the EKG waveform. A mean pulse transit time, wrist PPG magnitude, and finger PPG magnitude were estimated using the last twenty seconds of data measured during each stage of the experiment. A set of sample results from these experiments are presented in FIG. 7.

According to the non-invasive blood pressure measurement method of oscillometry the point of maximum arterial pulsation occurs when the external arterial pressure is equal to the mean arterial pressure. In this regard, see Hughes et al, "Measurements of Young's Modulus of Elasticity of the Canine Aorta with Ultrasound," *Ultrasonic Imaging*, vol. 1, pp. 356-367, (1979), which is incorporated herein by reference.

Furthermore, the magnitudes of these volumetric pulsations are a function of the transmural pressure dependent arterial compliance. Based on FIG. 7, the maximum arterial pulsation, or maximum wrist PPG amplitude, occurs during stage three of the experiment which suggests that the external wrist sensor pressure is at or near mean arterial pressure. The pulse transit time data is directly correlated with the wrist sensor PPG amplitude data. This correlation suggests that 1) the change in pulse transit time is a function of the magnitude of transmural pressure applied to the ulnar artery by the wrist sensor housing and 2) this relationship, like PPG magnitude, appears to be governed by the non-linear compliance of the vessel wall.

The results presented in this section demonstrate that a reduction in transmural pressure imposed by the wrist sensor housing on an intermediate arterial segment of the transit path plays a significant role in determining the velocity of the propagating pulse along this path. Further, the magnitude of the change in pulse wave velocity depends on the transmural pressure of the arterial segment and that the change in pulse wave velocity appears inversely correlated to the variation in the non-linear compliance of the arterial segment underlying the sensor housing. This suggests that the variation in external arterial pressure through an alteration in the skin contact pressure applied by a sensor housing, band, or cuff is a powerful tool that can be used to predictably alter PTT and calibrate the relationship between PTT and arterial blood pressure.

Embodiments for Calibration Based on Externally-Applied Pressure

In accordance with the present invention, the fundamental concepts behind the calibration techniques described herein may be adapted and applied to traditional PTT measurement devices that utilize an EKG and a finger-tip photoplethysmogram (PPG) in a variety of ways. One unique PTT measurement device that may be used for implementing the novel calibration methodology that has been described, is the embodiment depicted in FIG. 2, and that has been described above. This device consists of twin in-line PPG sensors 20 and 22, one measuring the pulse arrival time at the ulnar artery of the wrist and the other the pulse arrival time at the digital artery at the base of the little finger. A PPG sensor 20 located at the wrist eliminates the need for the EKG, which is a well-known source of BP estimation error in traditional devices.

Modeling of the System

A lumped parameter model relating pulse wave velocity (pwv) in the arteries to the transmural pressure acting across the artery wall ($P_{tm}$) can be developed for the arterial transit path monitored by our in-line sensors by combining the Moens-Korteweg equation with Hughes' non-linear expression (in Hughes et al.) for the elastic modulus of the artery wall as given in Eqn. (1), where it has been assumed that both model parameters $pwv_0$ and k, which each represent different physiologic properties of the artery, are approximately constant across the physiologic pressure range.

$$pwv(t) = pwv_0 \exp(k \cdot P_{tm}(t)) \quad (1)$$

The transit time of the pressure pulse across an arterial segment of length $\Delta z$ can be derived from (1) as given in (2) where $PTT = \Delta z/pwv$.

$$PTT(t) = \frac{\Delta z}{pwv_0} \exp(-k \cdot P_{tm}(t)) \quad (2)$$

Figure 9:
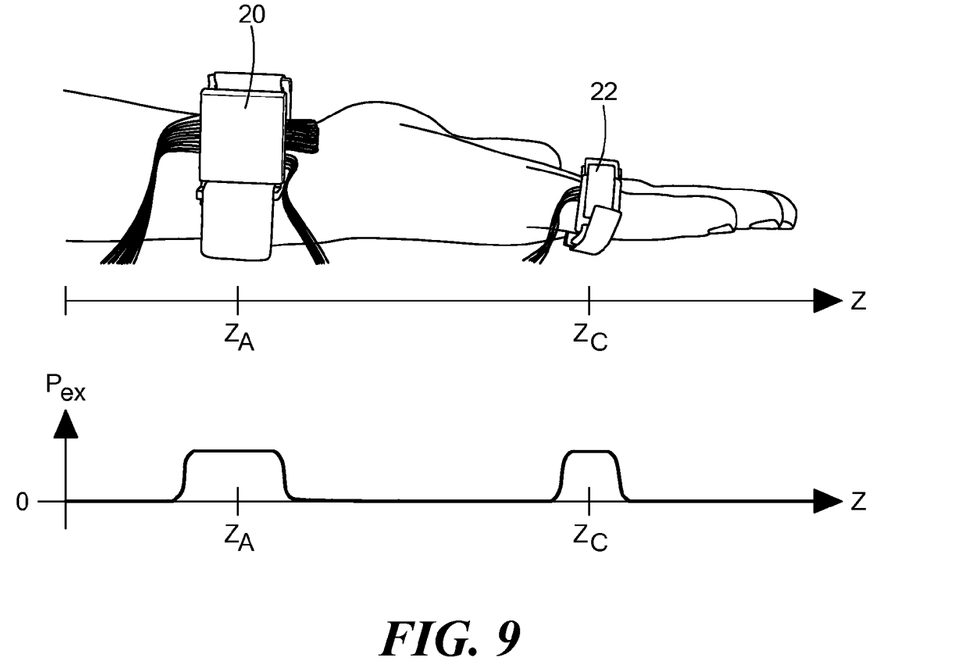
FIG. 9 shows a Twin PPG Sensor Pulse Transit Time Measurement Device, and a plot of the distributed external pressure, $P_{ex}$ acting along the arterial transit path that results from sensor contact pressure, in accordance with an embodiment of the present invention.

The two PPG sensor housings, each affixed to its respective measurement site with an adjustable elastic band, impose external pressure on the ulnar artery and digital artery wall, respectively, along the sensor contact area. External pressurization of the artery is necessary for arterial pulse waveform acquisition with the PPG. The external arterial pressure outside the sensor location areas is assumed to be negligible. A sketch of the distributed external pressure, $P_{ex}(z,t)$ along the arterial pulse transit path is shown along with the sensors 20 and 22 in FIG. 9, where $z_A$ denotes the measurement site of the wrist PPG signal and $z_C$ the measurement site of the finger PPG signal.

A distributed external pressure acting along the pulse transit path results in a distributed transmural pressure along the path as the internal blood pressure $P_{bp}(z,t)$, oscillates throughout the cardiac cycle. An expression for the distributed transmural pressure acting across the arterial wall along the pulse transit path is given in (3). The second term in the expression represents the effect of gravity on intravascular pressure where h(z,t) is the height of the transit path relative to the height of the heart, p the blood density, and g the gravitational acceleration constant.

$$P_{tm}(z,t) = P_{bp}(z,t) + \rho g h(z,t) - P_{ex}(z,t) \quad (3)$$

The distributed transmural pressure $P_{tm}$ acting along the pulse transit path between the two sensors located at sites $z_A$ and $z_C$ results in a distributed arterial compliance along the transit path which leads to a distributed pulse propagation velocity, $p\omega\upsilon(z,t)$ along the path.

Thus, an expression for the transit time of the pressure pulse between the two sensors requires integration (over the path) of this distributed pulse velocity as given in (4).

$$ptt(t, z_C - z_A) = \int_{z_A}^{z_C} \frac{1}{pwv_0} \exp(-k \cdot P_{tm}(z, t)) dz \quad (4)$$

Under the assumptions that the internal arterial blood pressure remains constant along the short propagation path $\partial P_{bp}/\partial z = 0$, and that the relative height is constant along the short transit path $\partial h/\partial z = 0$, a lumped parameter model can be used to approximate the pulse transit time in our distributed system by dividing the transit path into three segments each having an approximately uniform external pressure. The first arterial segment $\Delta z_A$ is under the influence of the external pressure applied by the wrist sensor housing $P_{ex,A}$, the second arterial segment $\Delta z_B$ is uninstrumented and has a negligible external pressure, and the third arterial segment $\Delta z_C$ is under the influence of an external pressure applied by the finger sensor housing, $P_{ex,C}$.

The lumped parameter model that expresses the relationship between PTT and the distributed transmural pressure in our twin PPG device is given in (5).

$$PTT(t) = \frac{\Delta z_A}{pwv_0} \exp(-k(P_{bp}(t) + \rho g h(t) - P_{ex,A})) + \frac{\Delta z_B}{pwv_0} \exp(-k(P_{bp}(t) + \rho g h(t))) + \frac{\Delta z_C}{pwv_0} \exp(-k(P_{bp}(t) + \rho g h(t) - P_{ex,C})) \quad (5)$$

An Embodiment Employing a Distributed Model

Figure 8:
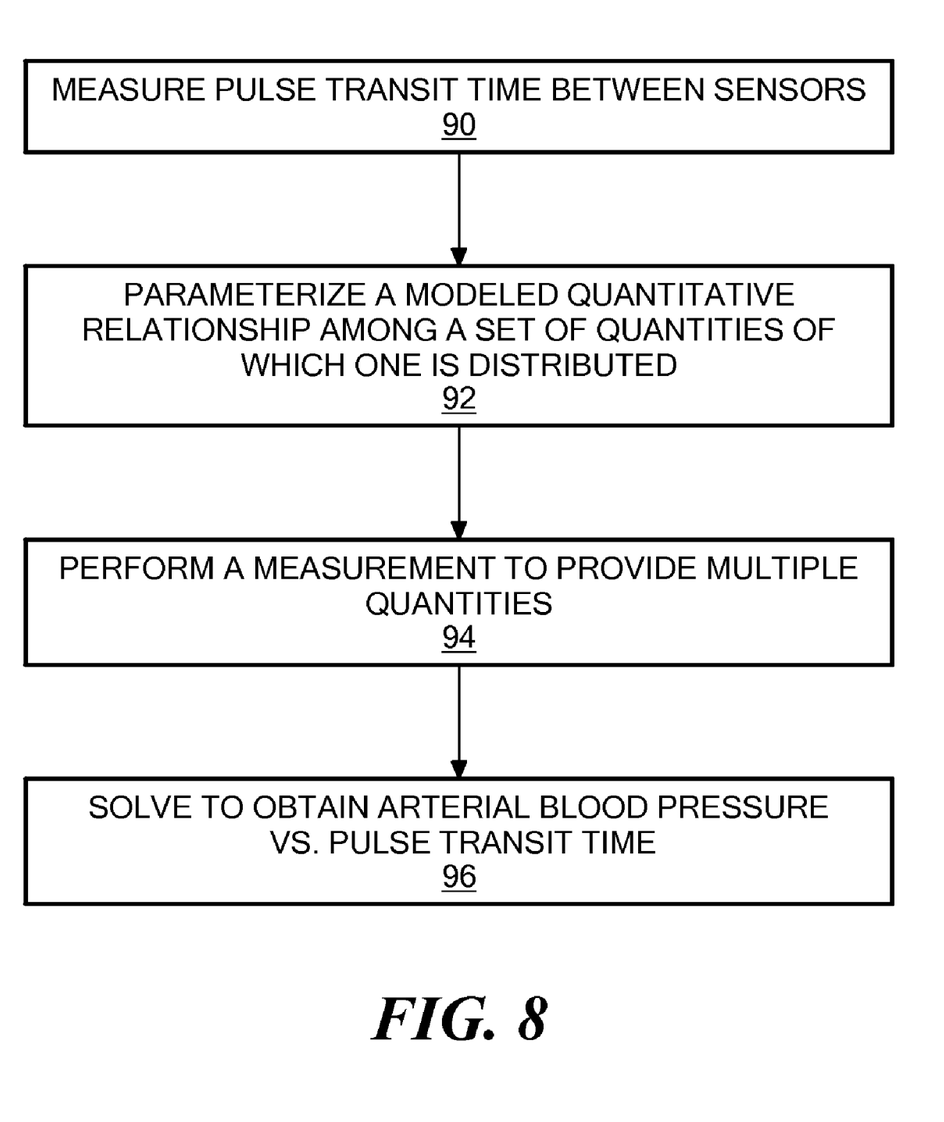
FIG. 8 is a flowchart illustrating a method for autonomous calibration of a pulse-transit-time monitoring device for measurement of arterial blood pressure in accordance with an embodiment of the present invention.

A method for autonomous calibration of a pulse-transit-time monitoring device for measurement of arterial blood pressure is now described with reference to the flowchart shown in FIG. 8.

A pulse transit time of a circulatory feature between a proximal sensor position and a distal sensor position disposed along a single arterial transit path on a human body is measured (step 90). The circulatory feature that is measured may be one or more of: transmural pressure, pulse wave velocity, arterial blood pressure, vertical height of all loci along the transit path, and any external pressure on a body surface along the transit path.

A modeled quantitative relationship among a set of quantities is parameterized 92, in such a way that at least one of which quantities is a quantity distributed with distance along the transit path. A measurement is performed 94 so as to provide a plurality of quantities from among the set of quantities. The plurality of quantities is then solved 96, on the basis of the modeled quantitative relationship, so as to obtain the arterial blood pressure as a function of the measured pulse transit time.

Where the distributed quantity, which may be arterial stiffness or compliant, or another quantity, is considered in distinct segments of the transit path, it may be assumed to be a function that is invariant over the transit path, although it may assume values that vary along the path.

An Embodiment Employing External Pressure Variation to Calibrate PTT to BP

A simple example can be used to explain how external pressure variation can serve as a means to calibrate PTT to BP. First, it is assumed that an arterial segment of length $\Delta z$ lying along the pulse transit path between the two sensors has been externally pressurized using an elastic band or cuff that applies an external pressure to the artery. To simplify this analysis, it is also assumed that the height of the transit path remains at heart level (h(t)=0) and that the length of the pulse transit path underlying the sensors is negligibly small ($\Delta z_A \approx \Delta z_C \approx 0$). The expression given in equation (5) can be transformed into the expression given in (6) where $l = \Delta z_B - \Delta z$ and $P_{ex}(t)$ is the external arterial pressure acting on the banded arterial segment.

$$PTT(t) = \frac{l}{pwv_0} \exp(-k \cdot P_{bp}(t)) + \frac{\Delta z}{pwv_0} \exp(k \cdot (P_{bp}(t) - P_{ex}(t))) \quad (6)$$

It is assumed that the external pressure acting on the arterial segment underlying the band at time $t_1$ is a constant value $P_{ex}(t=t_1) = P_1$. At a later time $t_2$, the circumference of the elastic band or cuff is decreased such that it applies a larger external pressure $P_{ex}(t=t_2) = P_2$ to the underlying artery. Assuming that blood pressure remains constant between the two external pressure stages, then the difference between the pulse transit time, $PTT_1$ measured under external pressure $P_1$ and the pulse transit time $PTT_2$ measured under external pressure $P_2$ is given in (7).

$$PTT_2 - PTT_1 = \frac{\Delta z}{pwv_0} \exp(-k(P_{bp} - P_2)) + \frac{\Delta z}{pwv_0} \exp(-k(P_{bp} - P_1)) \quad (7)$$

If the length of the transit path $\Delta z$ underlying the band is known, then the model parameters k and $pwv_0$ can be identified if the transmural pressure acting across the vessel wall underlying the banded segment is known $P_{bp} - P_i$, i=1,2. However, because there are two unknown model parameters, a minimum of two difference equations of the form given in (7) are required, in other words a third external pressure/transmural pressure value is required for identification of both parameters. In order to identify just one of the two parameters using known transmural pressure values only a single difference equation is required.

In an alternate embodiment of the invention, if only the external pressures in (7), $P_1$ and $P_2$, acting on the artery can be measured, then the model parameter k can be identified using external pressure variation. The external pressure acting on an artery can be measured through the use of a pressure sensor imbedded in the band or cuff which has the capability to measure the contact pressure that the band or cuff is applying to the skin surface. Assuming the arterial blood pressure remains constant between the two external pressure stages the difference equation in (7) can be transformed into the expression given in (8) which contain the unknown parameter k and the measured variables $PTT_1$, $PTT_2$, $P_1$, $P_2$, band length $\Delta z$ and total transit distance l. It should be noted that the external pressure required to identify the model parameter k can be much less than the pressure values required by an oscillometric cuff.

$$\frac{PTT_2}{PTT_1} = \frac{\left(\frac{l}{\Delta z} - 1\right) + \exp(k \cdot P_2)}{\left(\frac{l}{\Delta z} - 1\right) + \exp(k \cdot P_1)} \tag{8}$$

However, in order to achieve complete calibration for blood pressure estimation using external pressure variation, the model parameter $pwv_0$ must initially be identified through the one-time use of an alternative technique such as oscillometry.

Implementation using Wrist and Finger PPG Sensors

Although pressurization of an intermediate arterial segment is possible using a band or cuff, with the traditional EKG to PPG based sensor architecture, or potentially with in-line PPG sensors place at alternative locations, the dual PPG sensor architecture with a PPG sensor located at the wrist and finger base makes it difficult to pressurize an intermediate arterial segment along the transit path. However, it is possible to alter the external pressure at either of the two end segments of the transit path by varying the contact pressure applied by the sensor housings where the simplifying assumption given in the above example—that the transit path underlying the sensor housing is negligible—can be removed.

During device attachment the PPG sensor housings are affixed to the patient's wrist and finger base using adjustable elastic bands that apply an external arterial pressure $P_{ex,A}$ and $P_{ex,C}$ respectively. This type of attachment allows the patient to alter the external pressure applied by either of the sensor housings by simply adjusting the tension in either of the elastic sensor bands by altering the circumference of the band.

If the external pressure applied to the ulnar artery by the wrist sensor housing is at an initial value $P_{ex,A}=P_1$ at time $t_1$ and then is increased to a value $P_{ex,A}=P_2$ at time $t_2$ the expression in (5) can be reduced to the difference equation given in (9).

$$PTT_2 - PTT_1 = \frac{\Delta z_A}{pwv_0}\exp(-k(P_{bp} - P_2)) + \frac{\Delta z_A}{pwv_0}\exp(-k(P_{bp} - P_1)) \tag{9}$$

Figure 10:
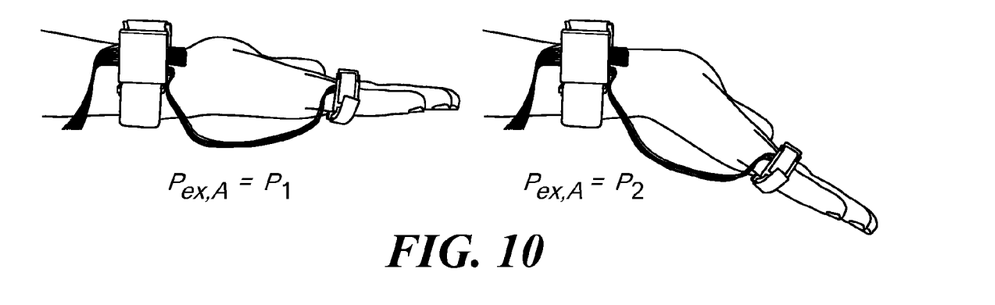
FIG. 10 depicts variation in hand posture altering the wrist sensor contact pressure, in accordance with embodiments of the present invention.

In alternate embodiments of the present invention, the external pressure variation may be achieved by designing and developing a simple adjustable strap or through the use of an automated inflatable cuff. Until such a strap or cuff is designed we can demonstrate the proof that external pressure variation can be used as a calibration tool using natural human motion. The external pressure applied to the ulnar artery by the wrist PPG sensor can be altered by increasing the circumference of the wrist by adjusting the posture of the hand through wrist joint rotation as shown in FIG. 10. Therefore by varying the natural posture of the hand we can cause a shift in the external arterial pressure applied by the wrist sensor housing and observe a change in measured PTT as predicted in the difference equation given in (9) where $P_1$ represents the external pressure at the wrist before posture change and $P_2$ a larger external pressure after posture change.

Transmural Pressure Estimation at the Sensor Measurement Site

As described above, identification of $pwv_0$ using external pressure variation requires measurement of the transmural pressure acting across the arterial wall underlying the banded segment. Estimation of the transmural pressure can be achieved using the concepts behind oscillometry which estimates the transmural pressure by locating the zero transmural pressure point through an alteration of either the external or internal arterial pressure. This alteration can be achieved using an inflatable cuff which increases the external pressure above the mean arterial pressure or using height variation. The demonstration of concept provided in the present patent applies on the height variation method which has previously been taught in US Patent Publication No. 2008/0039731, which is incorporated herein by reference.

A method of utilizing height variation to identifying the transmural pressure applied across the artery wall underlying the PPG sensor housing has previously been described by Shaltis, et al, "A Hydrostatic Pressure Approach to Cuffless Blood Pressure Monitoring," 2004 26th Annual International Conference of the IEEE/EMBS, San Francisco, Calif., USA, Sep. 1-5, 2004, incorporated herein by reference. This method is based upon the principles of oscillometry. According to the oscillometric method the maximum volumetric pulsation in the artery occurs when the transmural pressure acting across the wall is zero. For a sensor at heart level this pressure is achieved when the external arterial pressure equals the mean arterial blood pressure ($P_{mean}$). The zero transmural pressure point for the arterial segments underlying the sensor housings can be reached and identified from the PPG sensor signal with sensor height variation. As the height of the sensor is altered relative to the heart the zero transmural pressure point can be identified as the height ($h_{max}$) at which the maximum PPG signal pulsations are observed. This relationship is given in equation (10).

$$P_{mean}(t) - P_{ex}(t) = \rho g h_{max}(t) \tag{10}$$

This technique can be used to identify the transmural pressure applied to the arterial segment underling both the wrist sensor housing, with the hand in either posture, and the finger sensor housing. Thus the transmural pressures in equation (9) can be estimated as given in (11a) and (11b).

$$P_{bp} - P_1 = P_{mean} - P_{ex}(t_1) = \rho g h_{max}(t_1) \tag{11a}$$

$$P_{bp} - P_2 = P_{mean} - P_{ex}(t_2) = \rho h g_{max}(t_2) \tag{11b}$$

Given three different transmural pressures, the zero pressure pulse wave velocity $pwv_0$ and slope parameter k can be identified using equation (9). However, given just two measurements we can identify only a single model parameter in equation (9) e.g. $pwv_0$.

Because the demonstration of this concept utilized hand posture to alter external pressure at the wrist, the ability to alter external pressure between three distinct values was very difficult and only two postures/external pressures were implemented in the calibration procedure. Therefore, an alternative method was used to identify the model parameter k required for blood pressure estimation. Future devices that utilize external pressure for calibration will implement a more sophisticated mechanism for altering external pressure that can accurately adjust the pressure between three different values and can eliminate the need for an additional procedure to estimate model parameter k. The height variation used to identify the transmural pressure can also be used to identify the slope model parameter k, as described by McCombie, et al., "Adaptive blood pressure estimation from wearable PPG sensors using peripheral artery pulse wave velocity measurements and multi-channel blind identification of local arterial dynamics," in *Proc. of the 28th IEEE International Engineering in Medicine and Biology Conference*, New York, N.Y., pp. 3521-3524, August 2006, and in McCombie, et al., "Adaptive Hydrostatic Blood Pressure Calibration: Development of a wearable, autonomous pulse wave velocity blood pressure monitor," in *Proc. of the 29th IEEE International Engineering in Medicine and Biology Conference*, Lyon, France, pp. 370-373, August 2007. Both of the foregoing references are incorporated herein by reference. This height variation procedure used to identify model parameter k is also a subject of US Patent Publication No. 2007/0055163, and it, too, is incorporated herein by reference. Using this procedure, $pwv_0$ is identified relative to the mean arterial pressure, thus the present calibrated model will estimate continuous mean arterial pressure values.

Once $pwv_0$ and k are identified, an initial BP estimate can be made using the identified variables to estimate the transit time through the unloaded arterial segment $\Delta z_B$ which is assumed to have a negligible external pressure. The initial BP estimate can then be used to identify the external pressures applied by the sensor housing (5).

Experimental Demonstration of an Embodiment of the Invention

Although a variety of methods exist in the literature for identifying the arrival or onset time of a measured PPG waveform in order to estimate PTT, and all are within the scope of the present invention. All PTT estimates presented in these results utilized the waveform minimum, which occurs at the end of diastole immediately preceding systole as the arrival time. Pulse transit time was estimated as the difference in arrival time between the digital artery PPG signal and the ulnar artery PPG signal.

Figure 11:
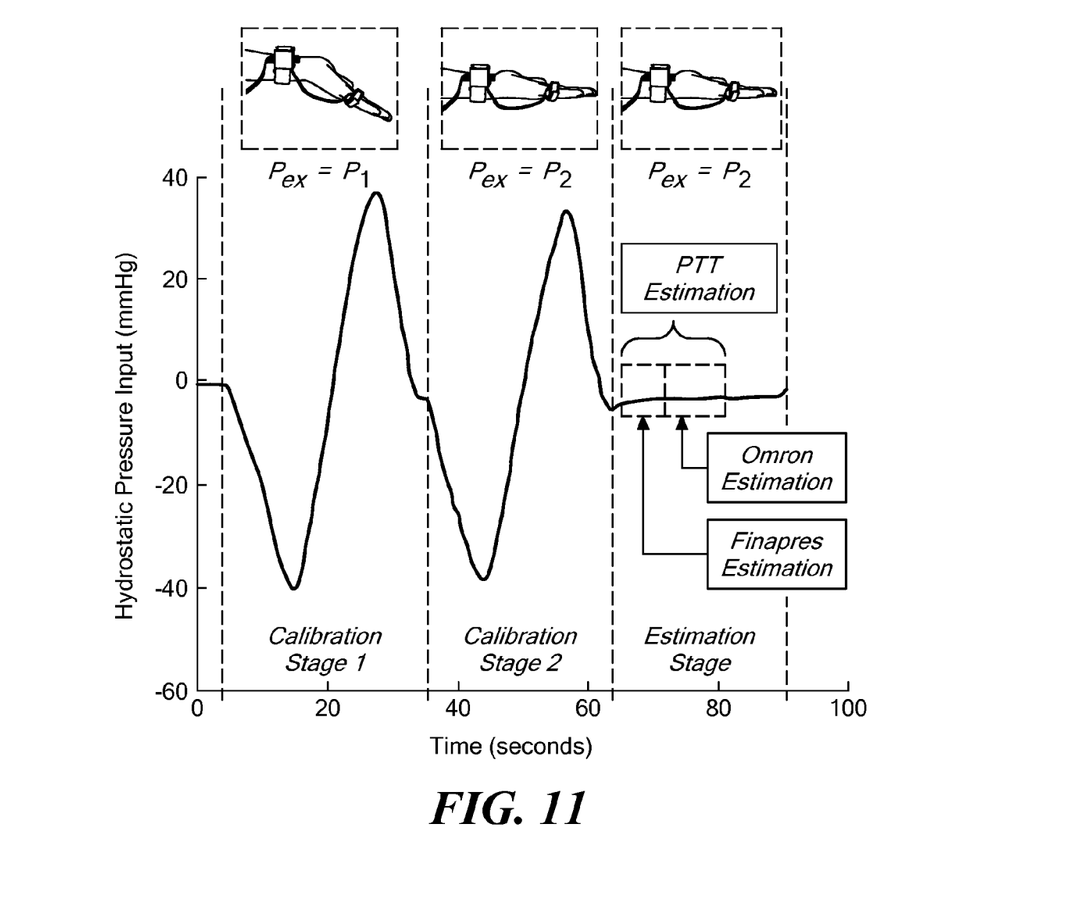
FIG. 11 shows sample intravascular pressure change estimated from arm height measurements during the full calibration human subject testing, in accordance with an embodiment of the present invention.

Human subject tests were performed to test the capability of a calibration algorithm that utilizes external arterial pressure variation to identify both model parameters k and $y_0$, and to estimate mean arterial blood pressure. During data collection a seated test subject was verbally instructed to raise and lower their hand above and below the level of the heart. The height change resembled a sine wave with a frequency of approximately 0.04 Hz. After completing 1-1.5 cycles of the arm height variation, the subject was instructed to alter the posture of the wrist in order to change the external pressure on the wrist sensor contact surface. After the posture change the subject was instructed to raise and lower their hand in a similar manner as before. Following the completion of 1-1.5 cycles of height variation the subject was instructed to rest their arm on a table at heart level. Once at rest a blood pressure measurement was taken on the arm opposite the PTT device using an Omron Hem 905 BP cuff for comparison with the PTT estimated mean arterial pressure. A sample of the height measurement data collected during one of the tests is shown in FIG. 11 and is marked with the various test periods and hand postures.

Figure 12:
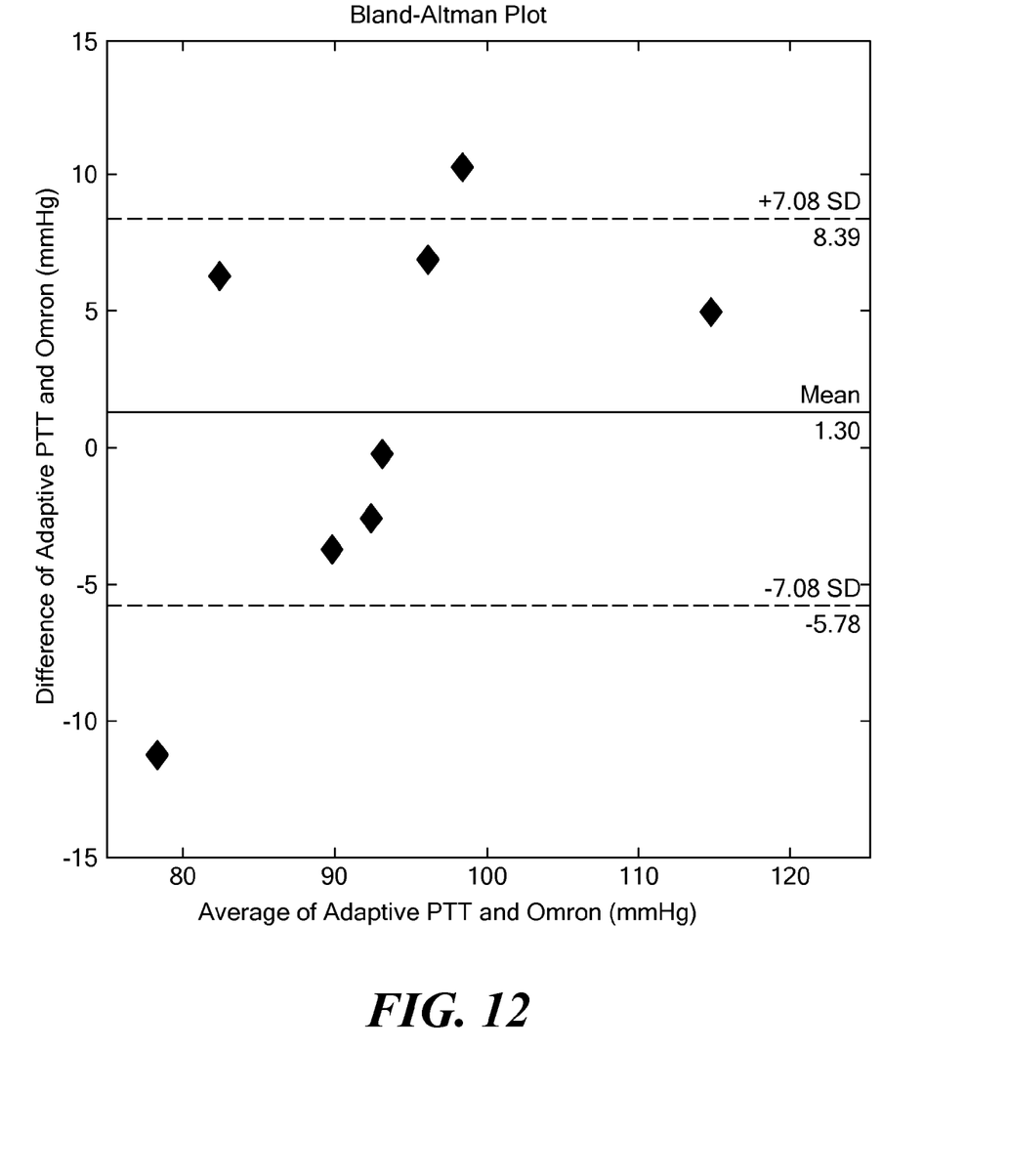
FIG. 12 plots a comparison of mean arterial pressure estimated with the calibrated PTT in accordance with an embodiment of the present invention versus mean arterial pressure estimated with an Omron® cuff.

The height variation was used to identify the transmural pressures acting across the arterial walls at the sensor measurement sites and to identify the model parameter k. The variation in external pressure between the two stages was used to identify the model parameter $pwv_0$ in equation (5). After identification of the two model parameters an initial mean arterial pressure estimate can be made and which allows the remainder of the unknown parameters in (5) to be identified. Given all the parameters in equation (5) this expression can be transformed to allow estimation of mean arterial blood pressure from future pulse transit time measurements Mean arterial blood pressure estimates made with the calibrated PTT were averaged over the 30 second period during which the Omron cuff was operating for comparison. A Bland-Altman plot displaying the results of the experiments is shown in FIG. 12. The PTT estimates show good agreement with the mean arterial pressure values estimated with the Omron cuff.

The embodiments of the invention that are described herein are intended to be merely exemplary and numerous variations and modifications will be apparent to those skilled in the art. All such variations and modifications are intended to be within the scope of the present invention as defined in the appended claims.

We claim:

1. A method for autonomous calibration of a pulse-transit-time monitoring device for measurement of arterial blood pressure, the method comprising:
    measuring a pulse transit time of a circulatory feature between a proximal sensor position and a distal sensor position, the proximal and distal sensor positions disposed along a single arterial transit path on a human body;
    parameterizing a modeled quantitative relationship among a set of quantities, at least one of which quantities is a quantity explicitly varying with distance along the transit path,
    wherein the transit path is treated in a lumped parameter model having at least three segments with respect to evaluation of the at least one quantity explicitly varying with distance along the transit path,
    wherein each quantity explicitly varying with distance along the transit path is a linear combination of terms, each term proportional to the length of each respective segment and an exponential function of the arterial blood pressure, and
    wherein the at least one quantity explicitly varying with distance is parametrized as a function of transmural pressure, pulse wave velocity, arterial blood pressure, vertical height of all loci along the transit path, and any external pressure on a body surface along the transit path;
    performing a measurement so as to provide a plurality of quantities from among the set of quantities; and
    solving the plurality of quantities, on the basis of the modeled quantitative relationship, so as to obtain the arterial blood pressure as a function of the measured pulse transit time.

2. A method in accordance with claim 1, wherein the quantity explicitly varying with distance along the transit path is parameterized as a function of external pressure.

3. A method in accordance with claim 1, wherein the quantity explicitly varying with distance is treated as a function that is invariant over the transit path.

4. A method, in accordance with claim 1, wherein the quantity distributed explicitly varying with distance is arterial stiffness.

5. A method in accordance with claim 1, wherein the step of measuring includes measuring a pressure.

6. A method in accordance with claim 5, wherein the step of measuring includes measuring an externally applied pressure.

7. A method, in accordance with claim 1, wherein the step of solving includes deriving a general dynamic relationship s(t) between a change in external pressure $\Delta P_{ex}(t)$, applied to an artery wall between the proximal sensor position and the distal sensor position, and a resulting change in pulse transit time $\Delta PTT(t)$.

8. A method in accordance with claim 1, wherein the set of quantities includes a plurality of quantities selected from the group including transmural pressure, pulse wave velocity, arterial blood pressure, vertical height of a plurality of loci along the transit path, and any external pressure on a body surface along the transit path.

9. A method in accordance with claim 1, wherein a first of the at least three segments corresponds to the proximal sensor position.

10. A method in accordance with claim 1, wherein a first of the at least three segments corresponds to the distal sensor position.

11. A method in accordance with claim 1, wherein one of the at least three segments is an uninstrumented segment.

12. A method in accordance with claim 1, wherein the vertical height of all segments is assumed to be equal.

13. A method in accordance with claim 1, further comprising externally varying the transmural pressure at least at one position along the arterial path connecting the proximal sensor position and the distal sensor position.

14. A method in accordance with claim 13, wherein a position at which the transmural pressure is varied is at the proximal sensor position.

15. A method in accordance with claim 13, wherein a position at which the transmural pressure is varied is at the distal sensor position.

16. A method in accordance with claim 13, wherein the transmural pressure is varied by means of a cuff.

17. A method in accordance with claim 13, wherein the transmural pressure is varied by varying body posture.

18. A method in accordance with claim 1, as above in which the quantified relationship is computed while the segments of the arterial path are moved through a plurality of heights.

19. A method in accordance with claim 13 or 18, further comprising remeasuring the pulse transit time of the circulatory feature between the proximal and distal sensor positions, subject to the externally varied transmural pressure.

20. A method in accordance with claim 19, further comprising applying the measured and remeasured pulse transit time to eliminate at least one model variable to obtain a calibrated measure of arterial blood pressure.

\* \* \* \* \*